(12) United States Patent
Guimaraes et al.

(10) Patent No.: US 11,779,729 B2
(45) Date of Patent: *Oct. 10, 2023

(54) CATHETER AND METHOD OF ENGAGING CATHETER

(71) Applicant: TERUMO KABUSHIKI KAISHA, Tokyo (JP)

(72) Inventors: Marcelo Guimaraes, Mount Pleasant, SC (US); Ryo Okamura, Fujinomiya (JP); Mitsuteru Yasunaga, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 326 days.

This patent is subject to a terminal disclaimer.

(21) Appl. No.: 17/116,390

(22) Filed: Dec. 9, 2020

(65) Prior Publication Data
US 2021/0085919 A1    Mar. 25, 2021

Related U.S. Application Data

(63) Continuation of application No. 16/357,626, filed on Mar. 19, 2019, now Pat. No. 10,946,170.

(51) Int. Cl.
*A61M 25/00* (2006.01)
*A61M 25/01* (2006.01)

(52) U.S. Cl.
CPC .... *A61M 25/0041* (2013.01); *A61M 25/0141* (2013.01); *A61M 25/008* (2013.01); *A61M 25/0054* (2013.01)

(58) Field of Classification Search
CPC .......... A61M 25/0041; A61M 25/0021; A61M 25/00; A61M 25/0043; A61M 25/01;
(Continued)

(56) References Cited

U.S. PATENT DOCUMENTS 5,322,509 A * 6/1994 Rickerd ............ A61M 25/0041
600/435
5,957,911 A    9/1999 Nesto
(Continued)

FOREIGN PATENT DOCUMENTS

CN    101384293 A    3/2009
EP    0850085 A1    7/1998
(Continued)

OTHER PUBLICATIONS

Optitorque ® Coronary Diagnostic Catheters, Terumo Interventional Systems, 4 pages, 2016 (month unknown), http://www.terumois.com/content/dam/terumopublic/products/optitorque/Optitorque-Brochure.pdf.
(Continued)

*Primary Examiner* — Jason E Flick
(74) *Attorney, Agent, or Firm* — BUCHANAN INGERSOLL & ROONEY PC

(57) ABSTRACT

A catheter for a hepatic artery introduced from an arm of a patient includes a first bent portion, a second bent portion distal of the first bent portion and bent to the same side as the first bent portion, a third bent portion disposed on a distal side of the second bent portion and bent to an opposite side from the second bent portion, and a most distal end portion disposed distal of the third bent portion, in which a minimum radius of curvature of the first bent portion is larger than a minimum radius of curvature of the second bent portion. The most distal end portion is directed to a common hepatic artery and the first bent portion comes into contact with an aorta wall on an opposite side from a celiac artery when the second bent portion contacts a blood vessel wall of the celiac artery.

19 Claims, 4 Drawing Sheets

(58) Field of Classification Search
CPC .......... A61M 25/0152; A61M 25/0141; A61M 25/0054; A61M 25/008
See application file for complete search history.

(56) References Cited

U.S. PATENT DOCUMENTS

| | | | |
|---|---|---|---|
| 6,039,723 A * | 3/2000 | Tanaka | A61M 25/0041 604/523 |
| 7,556,625 B2 | 7/2009 | Johnson | |
| 7,942,865 B2 | 5/2011 | Johnson | |
| 8,277,439 B2 | 10/2012 | Johnson | |
| 8,506,553 B2 | 8/2013 | Johnson | |
| 8,753,329 B2 | 6/2014 | Johnson | |
| 10,946,170 B2 | 3/2021 | Guimaraes et al. | |
| 2008/0306468 A1 | 12/2008 | Tamai et al. | |
| 2014/0276605 A1 | 9/2014 | Tejani et al. | |
| 2015/0273136 A1 | 10/2015 | Osiev | |

FOREIGN PATENT DOCUMENTS

| | | |
|---|---|---|
| EP | 3088035 A1 | 11/2016 |
| JP | 2000-271224 A | 10/2000 |
| JP | 3173720 U | 1/2012 |
| WO | 9709087 A1 | 3/1997 |
| WO | 2015146408 A1 | 10/2015 |

OTHER PUBLICATIONS

The European Search Report (Communication) dated Sep. 4, 2020, by the European Patent Office in corresponding European Patent Application No. 20164288.1-1132. (4 pages).

Guimaraes, et al., "Catheter and Method of Engaging Catheter", U.S. Appl. No. 16/816,829, filed Mar. 12, 2020.

Office Action (The First Office Action) dated Mar. 3, 2023, by the National Intellectual Property Administration, P. R. China in corresponding Chinese Patent Application No. 202010104894.4 and an English translation of the Office Action. (12 pages).

* cited by examiner

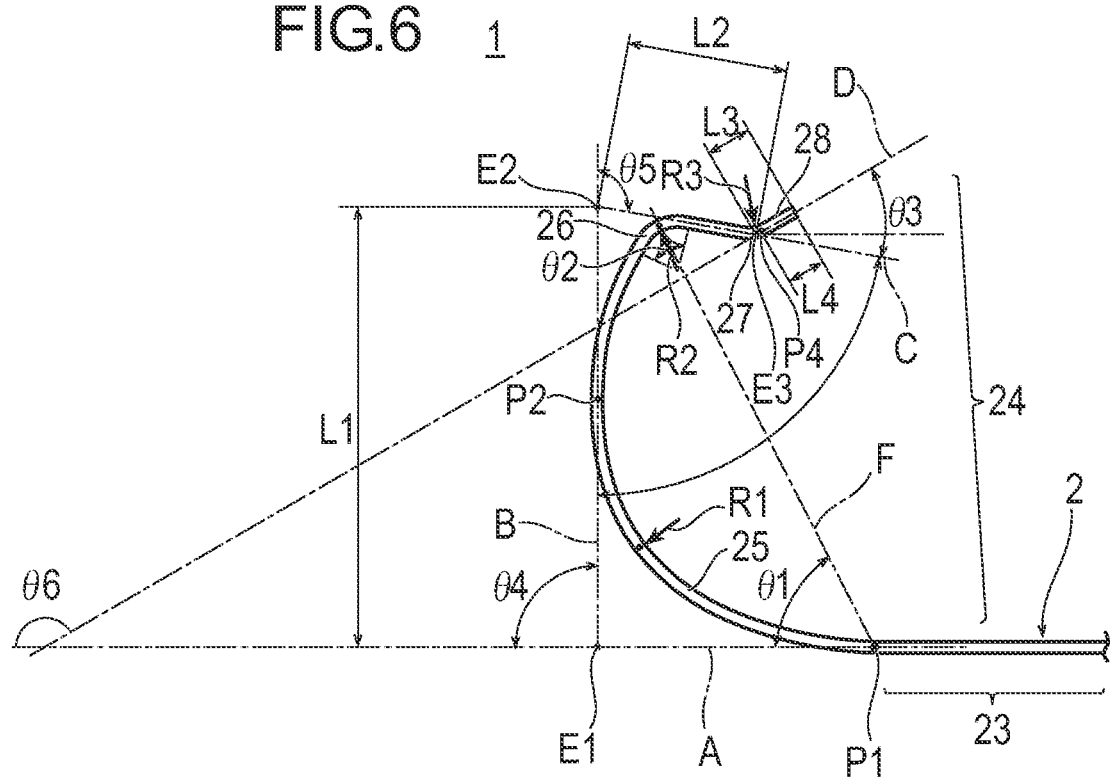
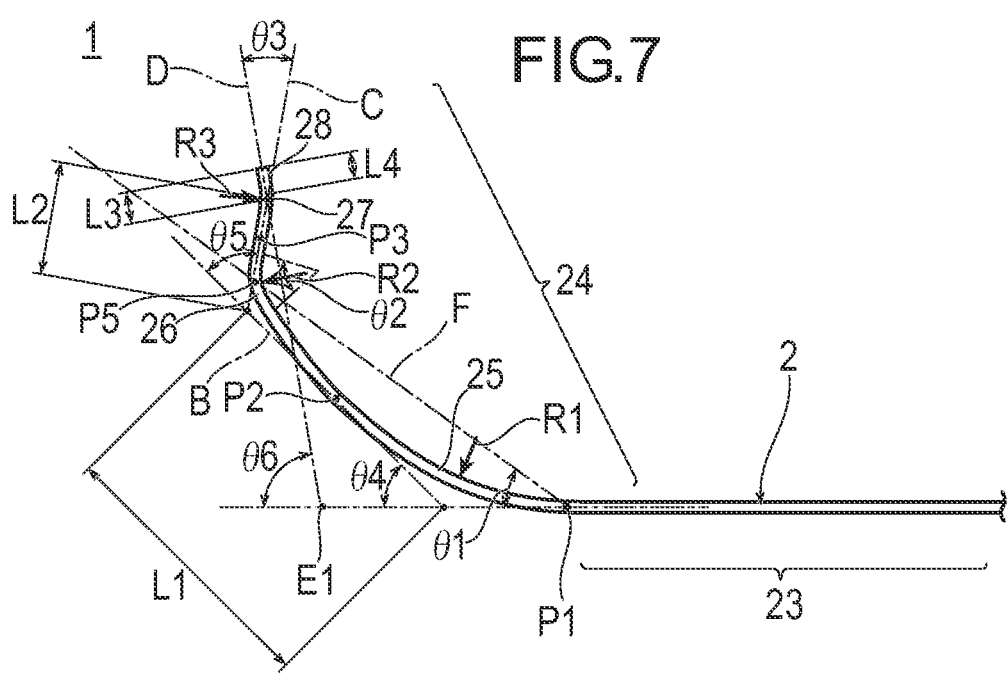

CATHETER AND METHOD OF ENGAGING CATHETER

CROSS REFERENCE TO RELATED APPLICATION

This application is a continuation application of U.S. application Ser. No. 16/357,626 filed Mar. 19, 2019, the entire content of which is incorporated herein in its entirety.

FIELD OF THE INVENTION

The present invention generally relates to a catheter inserted into a living body lumen and a method of engaging a catheter with a blood vessel.

BACKGROUND DISCUSSION

Currently, intervention has been carried out to perform treatment of a lesion area of the heart, a blood vessel, the liver, the brain, a digestive organ, a urinary organ, etc. using an elongated catheter inserted into a blood vessel from a puncture site in a patient's skin.

Recently, a technique for performing treatment by inserting a catheter from a radial artery of a wrist using trans radial intervention (TRI) has been performed. An example is disclosed in International Application Publication No. 2015/146408. Introducing a catheter from an artery of an arm reduces a physical burden of a patient and has an effect that the patient may be discharged from a hospital earlier.

When a lesion area is present in the liver, treatment for supplying an embolic agent or a medicine to the lesion area may be performed by a therapeutic catheter inserted to a vicinity of a hepatic artery in some cases. In such a treatment, it is desirable to use a guiding catheter so that the therapeutic catheter can sufficiently exert a function at a target position. The guiding catheter can provide a backup force to the therapeutic catheter to alleviate a reaction caused by insertion of the therapeutic catheter and to hold the therapeutic catheter at a desired position.

SUMMARY

As a guiding catheter for the hepatic artery to be introduced from the artery of the arm, for example, a guiding catheter for a coronary artery, etc. may be used. However, since the coronary artery and the hepatic artery have different shapes, operation is difficult. This same concern exists when using the guiding catheter for an artery other than the hepatic artery.

The catheter disclosed here is excellent in operability and a method of engaging the catheter.

According to one aspect, a catheter is configured catheter to be introduced into an arm of a patient and advanced to a hepatic artery of the patient. The catheter comprises a tubular body that includes a lumen extending from a proximal end of the tubular body to a distal end of the tubular body, the tubular body being comprised of a substantially linear main body portion and a shape portion that is bent so that an entirety of the shape portion is positioned in substantially the same plane. The shape portion comprises: a first bent portion disposed on a distal side of the main body portion, the first bent portion being bent toward one side and defining a first angle; a second bent portion disposed on a distal side of the first bent portion, the second bent portion being bent toward a side that is the same as the side to which the first bent portion is bent, the second bent portion defining a second angle; a third bent portion disposed on a distal side of the second bent portion, with the third bent portion being bent toward a side that is opposite the side to which the first and second bent portions are bent, the third bent portion defining a third angle; and a most distal end portion disposed on a distal side of the third bent portion. The first bent portion includes a smallest radius of curvature portion that possesses a smallest radius of curvature relative to a remainder of the first bent portion, wherein the second bent portion includes a smallest radius of curvature portion that possesses a smallest radius of curvature relative to a remainder of the second bent portion. The radius of curvature of the smallest radius of curvature portion of the first bent portion is larger than the radius of curvature of the smallest radius of curvature portion of the second bent portion. The most distal end portion is configured to be positioned in the common hepatic artery while the first bent portion is in contact with an aorta wall on an opposite side from a celiac artery and while the second bent portion is in contact with a blood vessel wall of the celiac artery. An axis passing through a center line of the main body portion is referred to as a first axis, the portion of the second bent portion having the smallest radius of curvature includes opposite ends and a second bending point representing a center point between the opposite ends, an axis passing through the second bending point and a first intermediate point positioned at a distal end of the main body portion is a fifth axis, and a first inclination angle between the fifth axis and the first axis is 34° to 63°.

In the catheter configured as described above, the first bent portion may come into contact with the aorta, the second bent portion may come into contact with the celiac artery, and the third bent portion may bend to the opposite side from the second bent portion so that the most distal end portion may be easily directed to the common hepatic artery. For this reason, an operator easily inserts another medical device into the common hepatic artery using the catheter as a guide.

The smallest radius of curvature of the first bent portion may be 10 to 80 mm, and the smallest radius of curvature of the second bent portion may be about 3 to 9 mm. In this way, the distal side of the catheter may be directed to the celiac artery by bending of the first bent portion, and the second bent portion more rapidly bending than the first bent portion may be appropriately brought into contact with the celiac artery.

The smallest radius of curvature of the first bent portion may be 10 mm to 80 mm, the smallest radius of curvature of the second bent portion may be about 3 mm to 9 mm, and a smallest radius of curvature of the third bent portion may be about 1 mm to 9 mm. In this way, the distal side of the catheter may be directed to the celiac artery by bending of the first bent portion, and the second bent portion more rapidly bending than the first bent portion may be appropriately brought into contact with the celiac artery. Further, the most distal end portion is relatively easily directed to the common hepatic artery in the celiac artery thinner than the descending aorta by the third bent portion more rapidly bent than the first bent portion in a direction opposite to the second bent portion.

The third angle may be more than 0° and 90° or less. In this way, when the second bent portion comes into contact with the celiac artery, the most distal end portion is easily directed to the common hepatic artery by the third bent portion bending at the third angle in a direction opposite to the second bent portion. For this reason, the catheter can easily guide another medical device to the common hepatic artery.

An axis passing through a center line of the main body portion may be referred to as a first axis, the portion of the second bent portion having the smallest radius of curvature includes opposite ends and a second bending point representing a center point between the opposite ends, and an axis passing through the second bending point and a first intermediate point positioned at a distal end of the main body portion is a fifth axis. A first inclination angle between the fifth axis and the first axis is 34° to 63°, and a second inclination angle constituting an angular range of the portion of the second bent portion having the smallest radius of curvature is 38° to 73°.

An axis passing through a center line of the main body portion may be referred to as a first axis, the portion of the second bent portion having the smallest radius of curvature includes opposite ends and a second bending point representing a center point between the opposite ends and an axis passing through the second bending point and a first intermediate point positioned at a distal end of the main body portion is referred to as a fifth axis. A first inclination angle between the fifth axis and the first axis is 46°, and a second inclination angle constituting an angular range of the portion of the second bent portion has the smallest radius of curvature is 73°.

A length of the most distal end portion may be 0.1 mm to 50 mm. In this way, the most distal end portion can be directed to the common hepatic artery with an appropriate length. For this reason, the catheter can easily guide another medical device to the common hepatic artery by the most distal end portion.

An effective length of the catheter may be 1,000 mm to 1,500 mm. In this way, the catheter can reach the celiac artery from the artery of the arm.

Another aspect of the disclosure here involves a catheter configured to be introduced into an arm of a patient and advanced to a hepatic artery of the patient. The catheter comprises a tubular body that includes a lumen extending from a proximal end of the tubular body to a distal end of the tubular body, wherein the tubular body is comprised of a substantially linear main body portion and a shape portion that is bent so that an entirety of the shape portion is positioned in substantially the same plane, with a distal end of the linear main body portion defining a first intermediate point. The shape portion comprises: a first bent portion disposed on a distal side of the main body portion, with the first bent portion being bent toward one side and defining a first angle; a second bent portion disposed on a distal side of the first bent portion, with the second bent portion being bent toward a side that is the same as the side to which the first bent portion is bent, and the second bent portion defining a second angle; a third bent portion disposed on a distal side of the second bent portion, with the third bent portion being bent toward a side that is opposite the side to which the first and second bent portions are bent, and the third bent portion defining a third angle; and a most distal end portion disposed on a distal side of the third bent portion. The first bent portion includes a smallest radius of curvature portion that possesses a smallest radius of curvature relative to a remainder of the first bent portion, the second bent portion includes a smallest radius of curvature portion that possesses a smallest radius of curvature relative to a remainder of the second bent portion, and the radius of curvature of the smallest radius of curvature portion of the first bent portion being larger than the radius of curvature of the smallest radius of curvature portion of the second bent portion. The most distal end portion is configured to be positioned in the common hepatic artery while the first bent portion is in contact with an aorta wall on an opposite side from a celiac artery and while the second bent portion is in contact with a blood vessel wall of the celiac artery. An axis passes through a center line of the main body portion is referred to as a first axis, and a central axis of the most distal end portion intersects the first axis at a point on the first axis that is distal of the first intermediate point.

The catheter is configured so that the first bent portion may come into contact with the descending aorta, and the second bent portion may be engaged with the celiac artery, so that the most distal end portion is easily directed to the common hepatic artery. For this reason, the operator easily inserts another medical device into the common hepatic artery using the catheter as a guide.

In a three-point bending test in which the tubular body is supported at two fulcrums and a center position of the two fulcrums is pushed from an opposite side by an indenter, a distance between fulcrums may be 25.4 mm, a fulcrum width of each fulcrum may be 4.0 mm, a radius of curvature of each fulcrum may be 2.0 mm, an indenter width may be 1.0 mm, a radius of curvature of the indenter may be 0.5 mm, a push amount by the indenter may be 2 mm, a temperature may be 25° C., and an indentation load acting on the indenter may be 20 to 250 gf in at least a part of the tubular body. When the tubular body is excessively stiff or rigid, it is difficult to insert the tubular body into a desired position and it is difficult to engage the tubular body to a predetermined place. When the tubular body is excessively flexible, the tubular body is likely to be disengaged even when the tubular body is engaged to a predetermined place. When the load is appropriate, the catheter is easily inserted and may be appropriately engaged.

A flexural modulus of at least a part of the shape portion may be 2 to 25 MPa. When the tubular body is excessively stiff or rigid, it is difficult to insert the tubular body into a desired position and it is difficult to engage the tubular body to a predetermined place. When the tubular body is excessively flexible, the tubular body is like to be disengaged even when the tubular body is engaged to a predetermined place. When the flexural modulus is appropriate, the catheter is easily inserted and may be appropriately engaged.

A portion in which a flexural property changes along a major axis of the tubular body may correspond to the shape portion. In this way, the shape portion is engaged to a predetermined place, and thus it is possible to set a desired flexural property.

A portion in which a flexural property changes along a major axis of the tubular body may correspond to the main body portion. In this way, the main body portion is inserted into a predetermined place, and thus it is possible to set a desired flexural property.

The tubular body may include a flexible portion at a distal side, the flexible portion having a bending characteristic of being more flexible than a proximal side, and a length of the flexible portion may be 500 mm or less. In this way, it is possible to reduce damage to a blood vessel in contact with the catheter.

An outer diameter of the tubular body may be 1 mm to 2.5 mm. In this way, the catheter can be introduced from the artery of the arm.

Still another aspect of the disclosure here involves a catheter configured to be introduced into an arm of a patient and advanced to a hepatic artery of the patient. The catheter comprises a tubular body that includes a lumen extending from a proximal end of the tubular body to a distal end of the tubular body, wherein the tubular body is comprised of a substantially linear main body portion and a shape portion that is bent so that an entirety of the shape portion is positioned in substantially the same plane. The shape portion comprises: a first bent portion disposed on a distal side of the main body portion, with the first bent portion being bent toward one side and defining a first angle; a second bent portion disposed on a distal side of the first bent portion, with the second bent portion being bent toward a side that is the same as the side to which the first bent portion is bent, the second bent portion defining a second angle; a third bent portion disposed on a distal side of the second bent portion, with the third bent portion being bent toward a side that is opposite the side to which the first and second bent portions are bent, the third bent portion defining a third angle; and a most distal end portion disposed on a distal side of the third bent portion. The first bent portion includes a smallest radius of curvature portion that possesses a smallest radius of curvature relative to a remainder of the first bent portion, the second bent portion includes a smallest radius of curvature portion that possesses a smallest radius of curvature relative to a remainder of the second bent portion, and the radius of curvature of the smallest radius of curvature portion of the first bent portion is larger than the radius of curvature of the smallest radius of curvature portion of the second bent portion. The most distal end portion is configured to be positioned in the common hepatic artery while the first bent portion is in contact with an aorta wall on an opposite side from a celiac artery and while the second bent portion is in contact with a blood vessel wall of the celiac artery. An axis passing through a center line of the main body portion is referred to as a first axis, and a plane passes through a first intermediate point positioned at a distal end of the main body portion and perpendicular to the first axis. The entirety of the first bent portion is located on a distal side of the first plane, an entirety of the second bent portion is located on a distal side of the first plane, an entirety of the third bent portion is located on a distal side of the first plane, and an entirety of the most distal end portion is located on a distal side of the first plane.

During use of the catheter, the most distal end portion may be directed to the second blood vessel by bringing the first bent portion into contact with the main artery and bringing the second bent portion into contact with the first blood vessel. For this reason, the operator can more easily insert another medical device into the second blood vessel using the catheter as a guide.

Also, the catheter may be introduced into a blood vessel from a distal radial artery, a conventional radial artery, an ulnar artery, a distal ulnar artery, a brachial artery, or a snuff box radial artery. In this way, the operator can introduce the catheter from various parts of the arm.

During use of the catheter, the main artery may be an aorta, the branched first blood vessel may be a celiac artery, and the selected second blood vessel may be a common hepatic artery. In this way, the operator can direct the most distal end portion to the common hepatic artery by bringing the first bent portion into contact with the aorta and bringing the second bent portion into contact with the celiac artery. For this reason, the operator can easily insert another medical device into the common hepatic artery using the catheter as a guide.

During use of the catheter, three blood vessel branching portions may be branched toward the periphery side. In this way, the operator can direct the most distal end portion to the second blood vessel selected from three blood vessels.

BRIEF DESCRIPTION OF THE DRAWINGS

FIG. 6 is a plan view illustrating a first modification of the catheter.

FIG. 7 is a plan view illustrating a second modification of the catheter.

DETAILED DESCRIPTION

Figure 1:
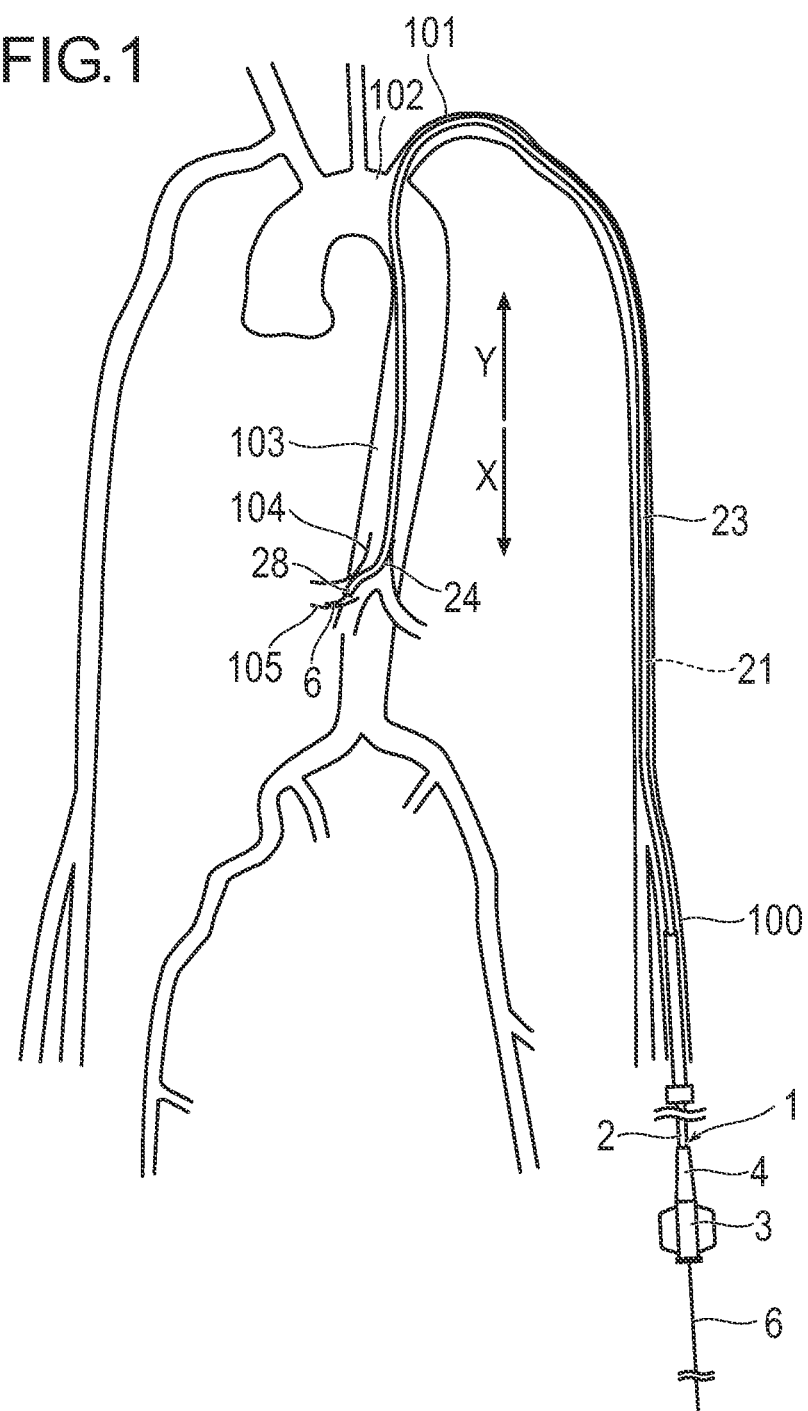
FIG. 1 is a schematic diagram illustrating arrangement of a catheter in a blood vessel.

Set forth below with reference to the accompanying drawings is a detailed description of embodiments of a catheter and a method of engaging a catheter in a blood vessel representing examples of the inventive catheter and catheter engaging method disclosed here. The dimensions or scales on the drawings may be exaggerated or different from actuality/reality for convenience of description and illustration. In addition, in this specification and the drawings, elements or features having substantially the same function are identified by the same reference numerals, and a detailed description of such features or aspects is not repeated. In this specification, a side or end of the catheter inserted into a lumen is referred to as a "distal side", and a hand side of the catheter to be operated is referred to as a "proximal side".

Figure 5:
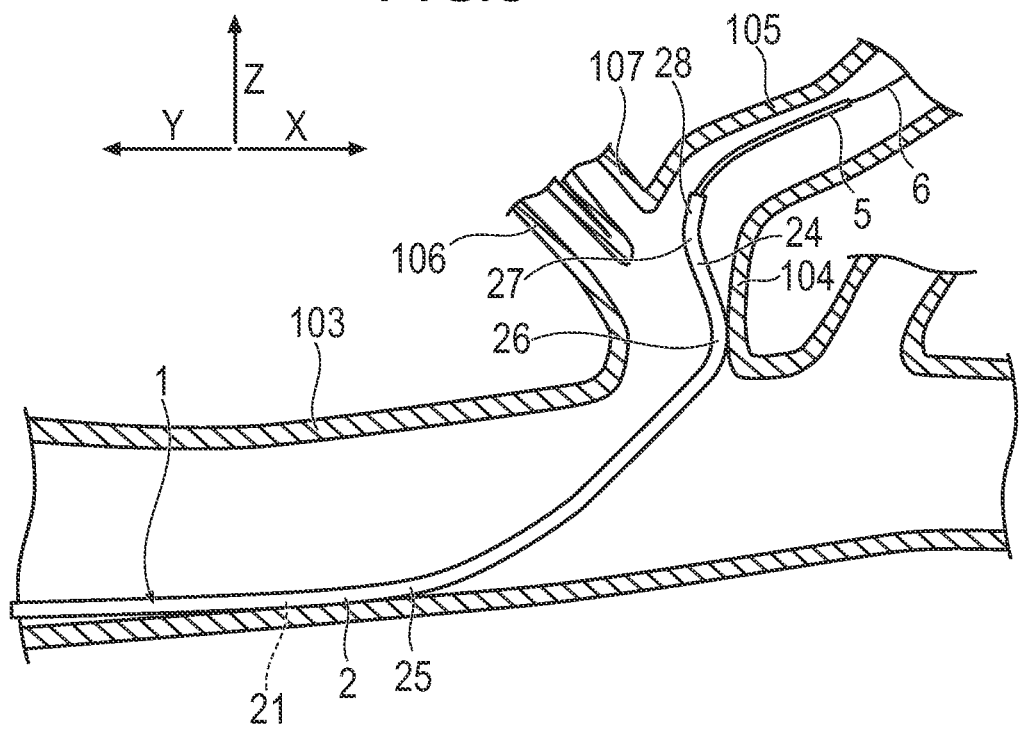
FIG. 5 is a schematic diagram illustrating a state in which the catheter is inserted into or positioned in a celiac artery.

As illustrated in FIGS. 1 and 5, a catheter 1 according to the present embodiment is a catheter for reaching a common hepatic artery 105. The catheter 1 is introduced into a blood vessel from an artery 100 (for example, a radial artery) of an arm of a patient and directed to a vicinity of the hepatic artery. The catheter 1 may correspond to a so-called guiding catheter, an angiography catheter, a guide wire support catheter or a microcatheter. Alternatively, the catheter 1 may correspond to a combination of a guiding catheter and a microcatheter which is inserted into an inner tube of the guiding catheter and longer than the guiding catheter.

The catheter 1 has a tubular body 2, a hub 3 disposed on a proximal side of the tubular body 2, and an anti-kink protector 4.

Figure 2:
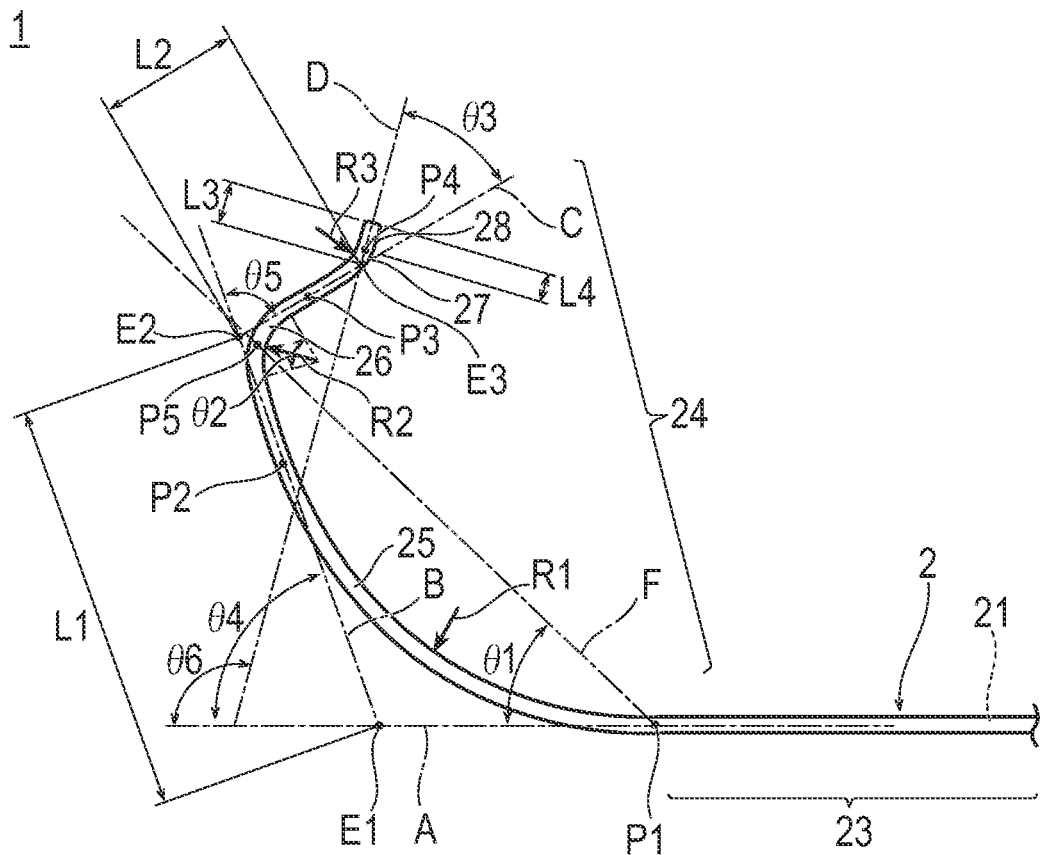
FIG. 2 is a plan view illustrating a distal end portion of the catheter according to an embodiment.

As illustrated in FIGS. 1 and 2, the tubular body 2 is elongated and is flexible. The tubular body 2 includes an approximately centrally located (centrally as seen with reference to a cross-section perpendicular to the central axis of the tubular body) lumen 21 extending from a proximal end of the tubular body to a distal end of the tubular body.

A passage communicating with the lumen 21 is formed in the hub 3. For example, the hub 3 can be used to insert or withdraw a guidewire 6, the therapeutic catheter 5, etc. In addition, the hub 3 can be used to inject various liquids such as an X-ray contrast medium, a chemical liquid, and a physiological saline solution.

The anti-kink protector 4 is formed of an elastic material. The anti-kink protector 4 covers a portion where the tubular body 2 and the hub 3 are connected. That is, the anti-kink protector 4 overlies the connection portion between the tubular body 2 and the hub 3. As a result, the anti-kink protector 4 prevents bending and kinking of the tubular body 2 in a vicinity of the connection portion.

The tubular body 2 will be described in detail. The tubular body 2 has a substantially linear main body portion 23 and a shaped shape portion 24. The shape portion 24 is curved in substantially the same plane. That is, the entirety of the shape portion 24 lies in substantially the same plane so that parts of the shape portion 24 that are curved or bent are curved or bent in that plane. The shape portion 24 has a first bent portion 25, a second bent portion 26, a third bent portion 27, and a most distal end portion 28. The first bent portion 25 extends from the linear main body portion 23 and is bent in the plane while extending in a distal direction from a first intermediate point P1 positioned at a distal end of the main body portion 23. The second bent portion 26 is bent in the plane and is bent in the same direction as that of the first bent portion 25 while extending in the distal direction from a second intermediate point P2 located at a distal end of the first bent portion 25. The second intermediate point P2 corresponds to or is located at a portion having a largest radius of curvature between the first bent portion 25 and the second bent portion 26. When the portion having the largest radius of curvature has a predetermined range along a center line of the tubular body 2 between the first bent portion 25 and the second bent portion 26, for example, the second intermediate point P2 can be defined as a center of that predetermined range along the center line. The third bent portion 27 is bent in the plane in an opposite direction to that of the second bent portion 26 while extending in the distal direction from a third intermediate point P3 located at a distal end of the second bent portion 26. The third intermediate point P3 corresponds to or is located at a portion having a largest radius of curvature between the second bent portion 26 and the third bent portion 27. When the portion having the largest radius of curvature has a predetermined range along the center line of the tubular body 2 between the second bent portion 26 and the third bent portion 27, for example, the third intermediate point P3 can be defined as a center of the predetermined range along the center line. The most distal end portion 28 linearly extends in the distal direction from a fourth intermediate point P4 located at a distal end of the third bent portion 27. The fourth intermediate point P4 is located at a proximal end of the most distal end portion 28 having a substantially linear or straight shape. The expression "curved in substantially the same plane" may include a case in which the distal end portion of the catheter 1 slightly protrudes from the plane to the extent that the same effect can be practically exerted or achieved in addition to the case in which the distal end portion of the catheter 1 is curved in the same plane.

An axis passing through a center line of the main body portion 23 is referred to as a first axis A. A tangent line of the center line of the tubular body 2 at the second intermediate point P2 is referred to as a second axis B. A tangent line of the center line of the tubular body 2 at the third intermediate point P3 is referred to as a third axis C. An axis passing through a center line of the most distal end portion 28 is referred to as a fourth axis D.

An angle formed between the second axis B and the first axis A at the distal side is defined as a first angle $\theta 4$. The first angle $\theta 4$ corresponds to a change amount in a direction of the center line of the tubular body 2 in the first bent portion 25. That is, the first bent portion 25 defines the first angle $\theta 4$. A radius of curvature of the first bent portion 25 may be constant throughout the first bent portion 25 or may change along the first bent portion 25. The first bent portion 25 includes a portion of the first bent portion having the smallest radius of curvature (a portion of the first bent portion 25 which is most abruptly bent or which has more curvature than any other part of the first bent portion 25), and this portion of the first bent portion 25 having the smallest radius of curvature possesses a radius of curvature R1 (first radius of curvature R1) that is preferably 10 to 80 mm, more preferably 15 to 60 mm, and even more preferably 20 to 55 mm. In an example of FIG. 2, the first radius of curvature R1 is 30 mm. The first angle $\theta 4$ is preferably 10° to 120°, more preferably 45° to 90°, and even more preferably 60° to 80°. In the example of FIG. 2, the first angle $\theta 4$ is 70°.

An angle formed between the third axis C and the second axis B at the distal side is defined as a second angle $\theta 5$. The second angle $\theta 5$ corresponds to a change amount in the direction of the center line of the tubular body 2 in the second bent portion 26. That is, the second bent portion 26 defines the second angle $\theta 5$. A radius of curvature of the second bent portion 26 may be constant throughout the second bent portion 26 or may change along the second bent portion 26. The second bent portion 26 includes a portion of the second bent portion having the smallest radius of curvature (a portion of the second bent portion 26 which is most abruptly bent or which has more curvature than any other part of the second bent portion 26), and this portion having the smallest radius of curvature possesses a radius of curvature R2 (second radius of curvature R2) that is preferably 3 to 9 mm, more preferably 4 to 8 mm, and even more preferably 4 to 6 mm. In the example of FIG. 2, the second radius of curvature R2 is 5 mm. The second angle $\theta 5$ is preferably 10° to 170°, more preferably 55° to 100°, and even more preferably 70° to 90°. In the example of FIG. 2, the second angle $\theta 5$ is 80°. The second radius of curvature R2 is smaller than the first radius of curvature R1.

An angle formed between the fourth axis D and the third axis C at the distal side is defined as a third angle $\theta 3$. The third angle $\theta 3$ corresponds to a change amount in the direction of the center line of the tubular body 2 in the third bent portion 27. That is, the third bent portion 27 defines the third angle $\theta 3$. A radius of curvature of the third bent portion 27 may be constant throughout the third bent portion 25 or may change along the third bent portion 27. The third bent portion 27 includes a portion of the third bent portion having the smallest radius of curvature (a portion of the third bent portion 27 which is most abruptly bent or which has more curvature than any other part of the third bent portion 27), and this portion having the smallest radius of curvature possesses a radius of curvature R3 (third radius of curvature R3) that is preferably 3 to 9 mm, more preferably 4 to 8 mm, and even more preferably 4 to 6 mm. In the example of FIG. 2, the third radius of curvature R3 is 5 mm. The third angle $\theta 3$ is preferably more than 0° and 90° or less, more preferably 20° to 70°, and even more preferably 30° to 60°. In the example of FIG. 2, the third angle $\theta 3$ is 45°.

An intersection between the first axis A and the second axis B is defined as a first intersection E1, an intersection between the second axis B and the third axis C is defined as a second intersection E2, and an intersection between the third axis C and the fourth axis D is defined as a third intersection E3.

A straight-line distance L1 between the first intersection E1 and the second intersection E2 is preferably 5 mm to 100 mm, more preferably 20 mm to 60 mm, and even more preferably 30 mm to 50 mm. In the example of FIG. 2, the straight-line distance L1 is 34 mm.

A straight-line distance L2 between the second intersection E2 and the third intersection E3 is preferably 1 mm to 80 mm, more preferably 5 mm to 50 mm, and even more preferably 10 mm to 20 mm. In the example of FIG. 2, the straight-line distance L2 is 12 mm.

A straight-line distance L3 between the third intersection E3 and a most distal end of the most distal end portion 28 is preferably 0.1 mm to 60 mm, more preferably 1 mm to 40 mm, and even more preferably 2 mm to 30 mm. In the example of FIG. 2, the straight-line distance L3 is 3.5 mm.

A length L4 along the center line of the most distal end portion 28 is preferably 0.1 mm to 50 mm, more preferably 0.5 mm to 30 mm, and even more preferably 1 mm to 20 mm. In the example of FIG. 2, the length L4 is 1.4 mm.

In the second bent portion 26, the center of the portion having the smallest radius of curvature (the peak of curvature) is defined as the second bending point P5. When the portion having the smallest radius of curvature has a predetermined range along the center line of the tubular body 2 in the second bent portion 26, for example, the second bending point P5 can be defined as a center of that range along the center line. An axis passing through the second bending point P5 and the first intermediate point P1 positioned at the distal end of the main body portion 23 is defined as a fifth axis F. An angle between the fifth axis F and the first axis A, at the distal side (i.e., on the distal side of the first intermediate point P1), is defined as a first inclination angle θ1. The first inclination angle θ1 is preferably 10° to 110°, more preferably 34° to 63°, and even more preferably 40° to 50°. In the example of FIG. 2, the first inclination angle θ1 is 46°. As the first inclination angle θ1 increases, the degree or amount of bending of the second bent portion 26 of the tubular body 2 increases.

A second inclination angle θ2 corresponds to the angular range of the portion of the second bent portion 26 having the second radius of curvature R2. That is, the second bent portion 26 has the second radius of curvature R2 in the range of the second inclination angle θ2 so that the second radius of curvature R2 extends over the angular range defined by the second inclination angle θ2. The second inclination angle θ2 is preferably 5° to 120°, more preferably 10° to 90°, and even more preferably 38° to 73°. In the example of FIG. 2, the second inclination angle θ2 is 73°.

An angle between the fourth axis D and the first axis A at the distal side is defined as a third inclination angle θ6. The third inclination angle θ6 is an angle formed by the most distal end portion 28 and the main body portion 23. The third inclination angle θ6 is preferably 0° to 240°, more preferably 80° to 150°, and even more preferably 90° to 120°. In the example of FIG. 2, the third inclination angle θ6 is 105°.

A reinforcement body may be buried or embedded in the tubular body 2, and the reinforcement body may extend over a range from the proximal end of the tubular body 2 to a predetermined position in the distal direction. The reinforcement body is formed by braiding a plurality of element wires into a tubular shape. A position of a most distal end of the reinforcement body is not particularly limited and is disposed in the shape portion 24 or the main body portion 23. For example, in a case where an outer diameter of the catheter 1 is 4 Fr, a shape of the catheter 1 may be difficult to hold without the reinforcement body, and thus the most distal end of the reinforcement body may be disposed in the shape portion 24 (for example, the first bent portion 25). In addition, in a case where the outer diameter of the catheter 1 is 5 Fr, the shape of the catheter 1 may be more easily held without the reinforcement body, and thus the most distal end of the reinforcement body may be disposed in the main body portion 23.

An outer diameter of the tubular body 2 is preferably 1 mm (3 Fr) to 2.5 mm (6 Fr), and more preferably 1.3 mm (4 Fr) to 1.8 mm (5 Fr). An effective length of the tubular body 2 (i.e., the length from the distal end of the anti-kink protector 4 to the distal end of the tubular body 2) is preferably 800 mm to 1,800 mm, more preferably 1,000 mm to 1,800 mm, and even more preferably 1,000 mm to 1,500 mm. The effective length can be still more preferably selected from 1,100 mm, 1,200 mm, 1,250 mm, and 1,300 mm depending on the physique of the patient or for a reason of insertion from a distal radial artery or a snuff box radial artery. It is preferable that the tubular body 2 can be appropriately selected depending on the patient, the blood vessel to be introduced, etc. For example, when the catheter 1 is introduced from a brachial artery of a small female, the effective length of the tubular body 2 is preferably relatively short. When the catheter 1 is introduced from a distal radial artery of a large male, the effective length of the tubular body 2 is preferably relatively long. The effective length is a length of a portion that can be inserted into a blood vessel, a sheath, etc. In the present embodiment, the effective length is a length from a most distal end of the anti-kink protector 4 to a most distal end of the tubular body 2.

The tubular body 2 has a flexible portion in which no reinforcement body is provided. This flexible portion is on the distal side of the reinforcement portion in which the reinforcement body is buried. By including the flexible portion, the catheter 1 can move in a bent or branched blood vessel without damaging the blood vessel. A length of the flexible portion is preferably 500 mm or less, and more preferably 10 mm to 200 mm. As an example, in the case of the 4 Fr catheter 1, the length of the flexible portion is 20 mm. In the case of the 5 Fr catheter 1, the length of the flexible portion is 150 mm. The flexible portion has a lower bending characteristic (i.e., is more easily bendable or more flexible) than that of the reinforcement portion. The bending characteristic may correspond to a flexural modulus, an actual measurement value of a load or a stress by a three-point bending test, etc. A flexural modulus of at least a part of the tubular body 2 is preferably 2 MPa to 25 MPa, more preferably 4 MPa to 20 MPa, even more preferably 7 MPa to 13 MPa, and still more preferably 9 MPa to 10 MPa. A load of the reinforcement portion by a three-point bending test is preferably 20 gf to 150 gf, and more preferably 40 gf to 120 gf. When the outer diameter of the catheter 1 is 4 Fr, the bending characteristic (load) is preferably 40 gf or more. When the outer diameter of the catheter 1 is 5 Fr, the bending characteristic (load) is preferably 80 gf or more.

Figure 3:
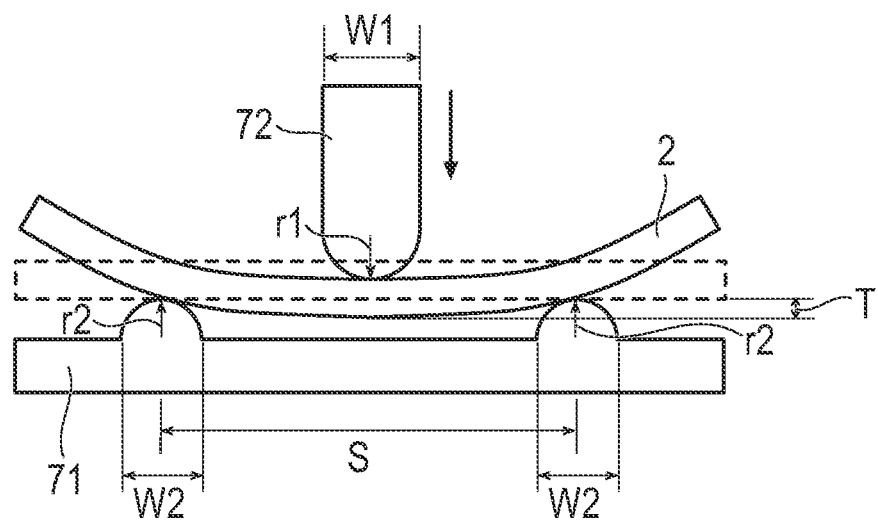
FIG. 3 is a plan view illustrating a three-point bending tester.

An example of measurement of the bending characteristic by the three-point bending test is illustrated in FIG. 3. As measurement conditions, for example, a temperature is 25° C., a distance S between fulcrums of a support base 71 is 25.4 mm (1 inch), a test speed of the indenter 72 that pushes a center position of the tubular body between the fulcrums (a position of the tubular body midway between the fulcrums) from the opposite side (the side of the tubular body opposite the side in contact with the fulcrums) is 5 mm/min, and a push amount T of the indenter 72 is 2 mm. An indenter width W1 is 1.0 mm, and a radius of curvature r1 of the indenter is 0.5 mm. A fulcrum width W2 of each fulcrum 73 of the support base 71 is 4.0 mm, and a radius of curvature r2 of each fulcrum 73 is 0.5 mm. An indentation load measured under these conditions can be used as the bending characteristic.

A length of the flexible portion is preferably 500 mm or less, and more preferably 10 mm to 200 mm. As an example, when the outer diameter of the catheter 1 is 4 Fr, the length of the flexible portion is 20 mm. When the outer diameter of the catheter 1 is 5 Fr, the length of the flexible portion is 150 mm.

In the tubular body 2, a distal tip which is more flexible than the proximal side may be disposed at a distal end portion. The distal tip is made of a flexible material such as a rubber material.

The number of layers included in the tubular body 2, a constituent material of each layer, the presence or absence of the reinforcement body, etc. may be different along a longitudinal direction of the tubular body 2.

Examples of a constituent material of the tubular body 2 include various thermoplastic elastomers such as styrene, polyolefin, polyurethane, polyester, polyamide, polybutadiene, trans-polyisoprene, fluororubber, and chlorinated polyethylene thermoplastic elastomers, polyether ketone, a polyimide-based material, etc., and it is possible to use one of these materials or a combination of two or more of these materials (a polymer alloy, a polymer blend, a laminate, etc.). A low friction material may be disposed on an inner peripheral surface of the tubular body 2 so that the guidewire 6 and other catheters, etc. can be easily inserted into and moved along the lumen 21. For example, the low friction material corresponds to a fluororesin material such as polytetrafluoroethylene (PTFE). The tubular body 2 may include an X-ray imaging material.

Next, a description will be given of a method of using the catheter 1 according to the present embodiment.

As illustrated in FIG. 1, the catheter 1 is inserted into the blood vessel from the artery 100 of the arm and is engaged with the celiac artery 104. For example, the artery 100 of the arm into which the catheter 1 is introduced corresponds to a distal radial artery, a conventional radial artery, an ulnar artery, a distal ulnar artery, a brachial artery, a snuff box radial artery, etc. Here, a case where the catheter 1 is inserted into an artery of a left arm will be described as an example. The catheter 1 may be inserted from an artery of a right arm.

In a procedure, an operator inserts the guidewire 6 into the artery 100 of the patient's arm. Subsequently, the operator introduces the proximal end of the guidewire 6 into the distal end of the catheter 1 and pushes the catheter 1 along the guidewire 6 while the guidewire 6 is accommodated in the lumen 21 of the catheter 1. Normally, the distal end of the guidewire 6 precedes the distal end of the catheter 1 (i.e., the distal end of the guidewire 6 extends distally beyond the most distal end of the catheter 1 while both are being advanced. Therefore, the shape portion 24 of the catheter 1 is deformed into a shape close to a straight line by the guidewire 6 in the lumen 21.

Figure 4:
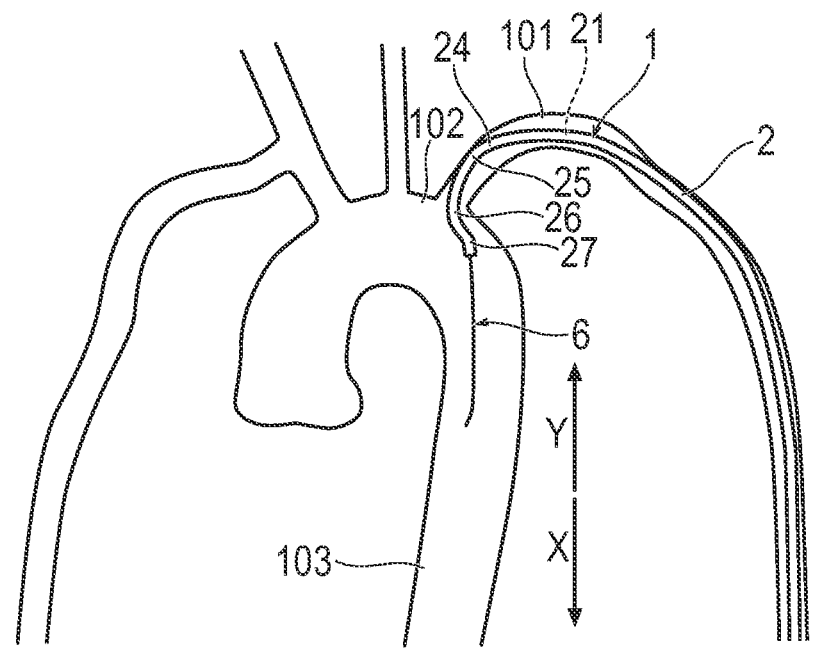
FIG. 4 is a schematic diagram illustrating a state in which the catheter is inserted into or positioned in a descending aorta.

As illustrated in FIG. 4, the guidewire 6 and the catheter 1 pass through the subclavian artery 101 and proceed to an aortic arch 102. At a portion where the subclavian artery 101 connects to the aortic arch 102, the catheter 1 needs to greatly bend to head toward the descending aorta 103. To deal with this fact, for example, the operator can temporarily move the guidewire 6 backward and accommodate the guidewire 6 in the lumen 21 of the catheter 1. In this way, the shape portion 24 of the catheter 1 is restored to an original bent shape. The operator can move the distal end of the catheter 1 forward from the aortic arch 102 toward the descending aorta 103 using the bending of the shape portion 24 (natural bending of the shape portion 24 when no force is applied to the shape portion 24 of the catheter). Thereafter, the operator causes the guidewire 6 to protrude distally from the catheter 1. That is, the operator relatively moves the guidewire 6 and the catheter 1 so that the distal end of the guidewire 6 extends distally beyond the most distal end of the catheter 1. In this way, the guidewire 6 can easily move forward to the descending aorta 103.

Subsequently, the operator pushes the catheter 1 along the guidewire 6. In this way, the catheter 1 can easily move forward from the aortic arch 102 to the descending aorta 103. The catheter 1 moves along the descending aorta 103 to a lower side X (a side close to a lower limb) and reaches a vicinity of the celiac artery 104.

After the guidewire 6 and the catheter 1 reach a vicinity of an entrance of the celiac artery 104, the operator moves the guidewire 6 backward to accommodate or position the guidewire 6 in the lumen 21 of the catheter 1 such that the most distal end of the guidewire 6 is positioned proximal of the most distal end of the catheter 1. In this way, as illustrated in FIG. 5, the shape portion 24 of the catheter 1 is restored to the original bent shape (i.e., the shape portion 24 returns to its natural bent state in which no force is applied to the shape portion 24). The operator can insert the distal end of the catheter 1 into the celiac artery 104 using the bending or bent configuration of the shape portion 24. The celiac artery 104 extends from the descending aorta 103 generally to a front side Z (ventral side). The common hepatic artery 105, a left gastric artery 106, and a splenic artery 107 branch off from the celiac artery 104. The common hepatic artery 105 generally extends from the celiac artery 104 to the lower side X (the side close to the lower limb). The left gastric artery 106 and the splenic artery 107 generally extend from the celiac artery 104 to an upper side Y (a side close to a head). As illustrated in FIG. 5, the second bent portion 26 of the catheter 1 contacts a blood vessel wall of the celiac artery 104, and the first bent portion 25 contacts a blood vessel wall of the descending aorta 103 on an opposite side from the entrance of the celiac artery 104. FIG. 5 also shows that the portion of the shape portion located distal of the second bent portion 26. The second bent portion 26 contacts a blood vessel wall on the lower side X of the celiac artery 104. In this way, the second bent portion 26 of the catheter 1 is engaged with the celiac artery 104. In this state, the third bent portion 27 is bent in a direction opposite to the direction of bend of the first bent portion 25 and the second bent portion 26. For this reason, the most distal end of the catheter 1 tends to be directed to the common hepatic artery 105 extending from the celiac artery 104 to the lower side X. The third bent portion 27 and/or the most distal end portion 28 may or may not come into contact with a blood vessel wall of the common hepatic artery 105.

Thereafter, the therapeutic catheter 5 longer than the catheter 1 is inserted into the lumen 21 of the catheter 1 from the hub 3. The operator can advance the therapeutic catheter 5 so that the therapeutic catheter 5 protrudes from or distally beyond the distal end of the catheter 1 and can easily insert the therapeutic catheter 5 into the common hepatic artery 105. In this instance, since the most distal end of the catheter 1 is directed from the celiac artery 104 to the lower side X, it is possible to suppress erroneous insertion of the therapeutic catheter 5 into the left gastric artery 106 or the splenic artery 107 directed to the upper side Y. Thereafter, the operator can insert the therapeutic catheter 5 into the common hepatic artery 105 and release an embolic agent or a drug solution via the therapeutic catheter 5. The catheter 1 alleviates or resists (counteracts) a reaction force caused by insertion of the therapeutic catheter 5. Further, the catheter 1 can apply a backup force to the therapeutic catheter 5 to hold the therapeutic catheter 5 at a desired position. A medical device to be inserted into the catheter 1 may not correspond to the therapeutic catheter 5. That is, medical devices other than the therapeutic catheter 5 may be used in the method discussed above.

Examples

Hereinafter, examples of the catheter and method disclosed here will be described. A catheter of Example 1 having an outer diameter of 4 Fr and a catheter of Example 2 having an outer diameter of 5 Fr were prepared. Each catheter was inserted from right and left radial arteries to verify a property of insertion from the subclavian artery into the descending aorta and a property of insertion into the celiac artery. The results are shown in Table 1, where ⊙ indicates excellent and ○ indicates good.

TABLE 1

|  | Outer diameter | Introduction position | Descending aorta | Celiac artery |
|---|---|---|---|---|
| Example 1 | 4 Fr | Left radial artery | ⊙ | ⊙ |
|  |  | Right radial artery | ○ | ⊙ |
| Example 2 | 5 Fr | Left radial artery | ⊙ | ⊙ |
|  |  | Right radial artery | ⊙ | ⊙ |

As a result, Example 1 having the outer diameter of 4 Fr was smoothly inserted when introduced from the left radial artery and inserted into the descending aorta 103 and then inserted into the celiac artery.

Even though Example 1 had a little difficulty when introduced from the right radial artery and inserted into the descending aorta, there was no problem in insertion into the celiac artery. In addition, Example 1 was smoothly inserted when introduced from the left radial artery and inserted into the descending aorta and then into the celiac artery.

Example 2 having the outer diameter of 5 Fr was smoothly inserted when introduced from the left radial artery and inserted into the descending aorta and then inserted into the celiac artery. Example 2 was smoothly inserted when introduced from the right radial artery and inserted into the descending aorta and when inserted into the celiac artery.

The invention is not limited only to the above-described embodiment, and various modifications can be made by those skilled in the art within a technical idea of the invention. For example, the catheter 1 can be appropriately designed within a range of various angles, dimensions, etc. described above. For example, as in a first modification illustrated in FIG. 6, the first inclination angle $\theta 1$ may be larger than that of the example illustrated in FIG. 2. In the first modification, the first inclination angle $\theta 1$ is 63°, the second inclination angle $\theta 2$ is 67°, the third inclination angle $\theta 6$ is 150°, the first radius of curvature R1 is 20 mm, the first angle $\theta 4$ is 90°, the second radius of curvature R2 is 4 mm, the second angle $\theta 5$ is 100°, the third radius of curvature R3 is 6 mm, the third angle $\theta 3$ is 40°, the distance L1 is 46 mm, the distance L2 is 17 mm, the distance L3 is 5 mm, and the length L4 is 2.9 mm. In the case of a type III case in which a brachiocephalic artery-aorta origin portion is disposed on a lower side (lower limb side) of a left common carotid artery-aorta origin portion, the catheter 1 of the first modification easily moves forward from a subclavian artery toward the descending aorta. Further, in a case where the celiac artery is directed upward (toward a heart), the catheter 1 of the first modification is more easily disposed in the celiac artery.

In addition, as in a second modification illustrated in FIG. 7, the first inclination angle $\theta 1$ may be smaller than that of the example illustrated in FIG. 2. In the second modification, the first inclination angle $\theta 1$ is 34°, the second inclination angle $\theta 2$ is 38°, the third inclination angle $\theta 6$ is 80°, the first radius of curvature R1 is 40 mm, the first angle $\theta 4$ is 45°, the second radius of curvature R2 is 6 mm, the second angle $\theta 5$ is 55°, the third radius of curvature R3 is 6 mm, the third angle $\theta 3$ is 20°, the distance L1 is 34 mm, the distance L2 is 14 mm, the distance L3 is 3.5 mm, and the length L4 is 2.4 mm. The catheter 1 of the second modification is easy to use for a patient having a small physique. Further, in a case where the celiac artery is directed downward (toward the lower limb side), the catheter 1 of the second modification is more easily disposed in the celiac artery.

In addition, the blood vessel with which the catheter 1 is engaged is not limited to the celiac artery 104. For example, the blood vessel with which the catheter 1 is engaged may correspond to a superior mesenteric artery, an inferior mesenteric artery, a renal artery, a lumbar artery, a splenic artery, a left gastric artery, a testicular artery, a common iliac artery, an internal iliac artery, a prostatic artery, a uterine artery, an external iliac artery, a coronary artery, etc.

The detailed description above describes a catheter and method of using a catheter representing examples of the inventive catheter and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter configured to be introduced into an arm of a patient and advanced to a hepatic artery of the patient, the catheter comprising
  a tubular body that includes a lumen extending from a proximal end of the tubular body to a distal end of the tubular body;
  the tubular body being comprised of a substantially linear main body portion and a shape portion that is bent so that an entirety of the shape portion is positioned in substantially the same plane;
  the shape portion comprising:
    a first bent portion disposed on a distal side of the main body portion, the first bent portion being bent toward one side and defining a first angle;
    a second bent portion disposed on a distal side of the first bent portion, the second bent portion being bent toward a side that is the same as the side to which the first bent portion is bent, the second bent portion defining a second angle;
    a third bent portion disposed on a distal side of the second bent portion, the third bent portion being bent toward a side that is opposite the side to which the first and second bent portions are bent, the third bent portion defining a third angle;
    a most distal end portion disposed on a distal side of the third bent portion;
    the first bent portion including a smallest radius of curvature portion that possesses a smallest radius of curvature relative to a remainder of the first bent portion, the second bent portion including a smallest radius of curvature portion that possesses a smallest radius of curvature relative to a remainder of the second bent portion, the radius of curvature of the smallest radius of curvature portion of the first bent portion being larger than the radius of curvature of the smallest radius of curvature portion of the second bent portion;

the most distal end portion being configured to be positioned in the common hepatic artery while the first bent portion is in contact with an aorta wall on an opposite side from a celiac artery and while the second bent portion is in contact with a blood vessel wall of the celiac artery;

an axis passing through a center line of the main body portion is referred to as a first axis;

the portion of the second bent portion having the smallest radius of curvature includes opposite ends and a second bending point representing a center point between the opposite ends;

an axis passing through the second bending point and a first intermediate point positioned at a distal end of the main body portion is a fifth axis; and a first inclination angle between the fifth axis and the first axis is 34° to 63°.

2. The catheter according to claim 1, wherein the smallest radius of curvature of the first bent portion is 10 mm to 80 mm, and the smallest radius of curvature of the second bent portion is 3 mm to 9 mm.

3. The catheter according to claim 1, wherein the smallest radius of curvature of the first bent portion is 10 mm to 80 mm, the smallest radius of curvature of the second bent portion is 3 mm to 9 mm, and a smallest radius of curvature of the third bent portion is 1 mm to 9 mm.

4. The catheter according to claim 1, wherein the third angle is more than 0° and 90° or less.

5. The catheter according to claim 4, wherein a second inclination angle constituting an angular range of the portion of the second bent portion having the smallest radius of curvature is 38° to 73°.

6. The catheter according to claim 1, wherein the first inclination angle is 46°, and a second inclination angle constituting an angular range of the portion of the second bent portion having the smallest radius of curvature is 73°.

7. The catheter according to claim 1, wherein a length of the most distal end portion is 0.1 mm to 50 mm.

8. The catheter according to claim 1, wherein an effective length of the catheter is 1,000 mm to 1,500 mm.

9. A catheter configured to be introduced into an arm of a patient and advanced to a hepatic artery of the patient, the catheter comprising
 a tubular body that includes a lumen extending from a proximal end of the tubular body to a distal end of the tubular body;
 the tubular body being comprised of a substantially linear main body portion and a shape portion that is bent so that an entirety of the shape portion is positioned in substantially the same plane;
 the shape portion comprising:
  a first bent portion disposed on a distal side of the main body portion, the first bent portion being bent toward one side and defining a first angle;
  a second bent portion disposed on a distal side of the first bent portion, the second bent portion being bent toward a side that is the same as the side to which the first bent portion is bent, the second bent portion defining a second angle;
  a third bent portion disposed on a distal side of the second bent portion, the third bent portion being bent toward a side that is opposite the side to which the first and second bent portions are bent, the third bent portion defining a third angle;
  a most distal end portion disposed on a distal side of the third bent portion;
 the first bent portion including a smallest radius of curvature portion that possesses a smallest radius of curvature relative to a remainder of the first bent portion, the second bent portion including a smallest radius of curvature portion that possesses a smallest radius of curvature relative to a remainder of the second bent portion, the radius of curvature of the smallest radius of curvature portion of the first bent portion being larger than the radius of curvature of the smallest radius of curvature portion of the second bent portion;
 the most distal end portion being configured to be positioned in the common hepatic artery while the first bent portion is in contact with an aorta wall on an opposite side from a celiac artery and while the second bent portion is in contact with a blood vessel wall of the celiac artery;
 an axis passing through a center line of the main body portion is referred to as a first axis;
 a plane passing through a first intermediate point positioned at a distal end of the main body portion and perpendicular to the first axis;
 an entirety of the first bent portion being located on a distal side of the first plane;
 an entirety of the second bent portion being located on a distal side of the first plane;
 an entirety of the third bent portion being located on a distal side of the first plane; and
 an entirety of the most distal end portion being located on a distal side of the first plane.

10. The catheter according to claim 9, wherein:
 the portion of the second bent portion having the smallest radius of curvature includes opposite ends and a second bending point representing a center point between the opposite ends;
 an axis passing through the second bending point and the first intermediate point positioned at the distal end of the main body portion is a fifth axis; and
 a first inclination angle between the fifth axis and the first axis is 34° to 63°.

11. The catheter according to claim 9, wherein the smallest radius of curvature of the first bent portion is 10 mm to 80 mm.

12. The catheter according to claim 9, wherein the smallest radius of curvature of the second bent portion is 3 mm to 9 mm.

13. The catheter according to claim 9, wherein a smallest radius of curvature of the third bent portion is 1 mm to 9 mm.

14. The catheter according to claim 9, wherein the third angle is more than 0° and 90° or less.

15. A catheter configured to be introduced into an arm of a patient and advanced to a hepatic artery of the patient, the catheter comprising
 a tubular body that includes a lumen extending from a proximal end of the tubular body to a distal end of the tubular body;
 the tubular body being comprised of a substantially linear main body portion and a shape portion that is bent so that an entirety of the shape portion is positioned in substantially the same plane, a distal end of the linear main body portion defining a first intermediate point;

the shape portion comprising:
- a first bent portion disposed on a distal side of the main body portion, the first bent portion being bent toward one side and defining a first angle;
- a second bent portion disposed on a distal side of the first bent portion, the second bent portion being bent toward a side that is the same as the side to which the first bent portion is bent, the second bent portion defining a second angle;
- a third bent portion disposed on a distal side of the second bent portion, the third bent portion being bent toward a side that is opposite the side to which the first and second bent portions are bent, the third bent portion defining a third angle;
- a most distal end portion disposed on a distal side of the third bent portion;
- the first bent portion including a smallest radius of curvature portion that possesses a smallest radius of curvature relative to a remainder of the first bent portion, the second bent portion including a smallest radius of curvature portion that possesses a smallest radius of curvature relative to a remainder of the second bent portion, the radius of curvature of the smallest radius of curvature portion of the first bent portion being larger than the radius of curvature of the smallest radius of curvature portion of the second bent portion;
- the most distal end portion being configured to be positioned in the common hepatic artery while the first bent portion is in contact with an aorta wall on an opposite side from a celiac artery and while the second bent portion is in contact with a blood vessel wall of the celiac artery;
- an axis passing through a center line of the main body portion is referred to as a first axis; and
- a central axis of the most distal end portion intersecting the first axis at a point on the first axis that is distal of the first intermediate point.

16. The catheter according to claim 15, wherein the smallest radius of curvature of the first bent portion is 10 mm to 80 mm.

17. The catheter according to claim 15, wherein the smallest radius of curvature of the second bent portion is 3 mm to 9 mm.

18. The catheter according to claim 15, wherein a smallest radius of curvature of the third bent portion is 1 mm to 9 mm.

19. The catheter according to claim 15, wherein the third angle is more than 0° and 90° or less.

* * * * *